United States Patent

Kefauver et al.

[11] Patent Number: 5,540,852
[45] Date of Patent: Jul. 30, 1996

[54] PERSONAL CLEANSING BAR WITH TAILORED FATTY ACID SOAP

[75] Inventors: Philip J. Kefauver, Loveland; Fernando R. Tolléns; Scott W. Syfert, both of Cincinnati, all of Ohio

[73] Assignee: The Procter & Gamble Company, Cincinnati, Ohio

[21] Appl. No.: 381,579

[22] Filed: Jan. 31, 1995

[51] Int. Cl.$^6$ .................. C11D 9/00; C11D 9/22
[52] U.S. Cl. .............. 510/152; 510/153; 510/154; 510/484; 510/491
[58] Field of Search ................... 252/108, 117, 252/121, 132, 134, 174.17, 174.23, 547, DIG. 16

[56] References Cited

U.S. PATENT DOCUMENTS

| | | | |
|---|---|---|---|
| 4,946,618 | 8/1990 | Knochel et al. | 252/117 |
| 5,387,362 | 2/1995 | Tollens et al. | 252/108 |

Primary Examiner—E. Rollins Cross
Assistant Examiner—Patricia L. Hailey
Attorney, Agent, or Firm—Tara M. Rosnell; Leonard Williamson

[57] ABSTRACT

The present invention relates to a mild, lathering personal cleansing soap bar composition by weight of the bar comprising: from 30 to 85 parts of tailored fatty acid soap, from 0 parts to 30 parts lathering synthetic detergent/surfactant, and from 5 to 35 parts of water. The tailored fatty acid soap comprises:

I. from 50% to 85% is saturated fatty acid soap selected from the group consisting of: myristic, palmitic, and stearic acid soaps and mixtures thereof; and II. from 15% to 50% is mixture of oleic (C18:1) and lauric acid (C12) soaps; including from 0 to 10% minor fatty acid soaps selected from the group consisting of: C8, C10, C18:2; and mixtures thereof;

wherein said tailored fatty acid soap is a mixture of 65% to about 95% sodium soap and from 5% to about 35% magnesium soap.

14 Claims, 2 Drawing Sheets

1

PERSONAL CLEANSING BAR WITH TAILORED FATTY ACID SOAP

TECHNICAL FIELD

This invention relates to personal cleansing bar soaps.

BACKGROUND OF THE INVENTION

The cleansing of skin with surface-active cleansing preparations has become a focus of great interest. Many people wash and scrub their skin with various surface-active preparations several times a day. An ideal skin cleanser should cleanse the skin gently, causing little or no irritation, without defatting or overdrying the skin or leaving it taut after frequent routine use. Most lathering skin cleansers, liquids and bars, fail in this respect.

Synthetic detergent bars, frequently referred to as "syndet bars," are well known and are becoming increasingly popular. However, widespread replacement of soap bars by syndet bars has not so far been possible for a variety of reasons, primarily the different physical characteristics of syndet bars as compared to soap bars, e.g., processability, cost, smear or bar messiness, lather and rinse negatives.

The skin cleansing art is much more complex in our time. To improve skin cleansing mildness without processing and/or lather negatives, can be an unobvious and delicate balancing act.

It will be appreciated that rather stringent requirements for skin cleansers limit the choice of surface-active agents and final formulations represent some degree of compromise. Mildness is often obtained at the expense of effective cleansing and lathering. Conversely, mildness may be sacrificed for either preferred lathering characteristics, rinse feel, bar firmness, product stability, or all of the above. To provide an improvement or fix a problem in this art is usually more than mere optimization of the known art. There is an infinite number of ways to blend and tailor fatty acid soaps and synthetic surfactants. Which tailored soap blend is useful for a particular product or process is not always predictable.

A search of the bar soap literature will attest to the fact that those skilled in the art are still making improvements in the skin cleansing art.

Figure 1:
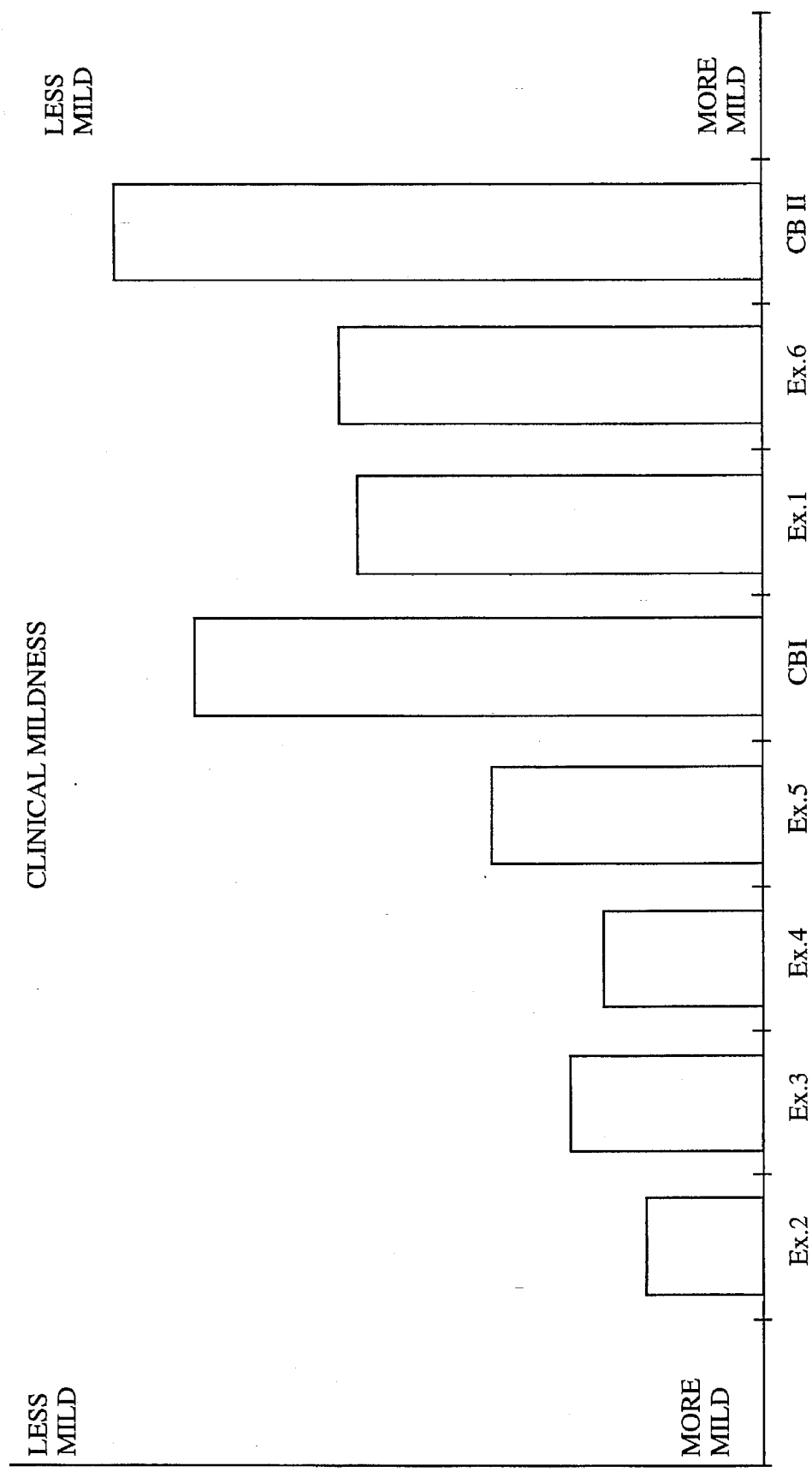
FIG. 1
Figure 2:
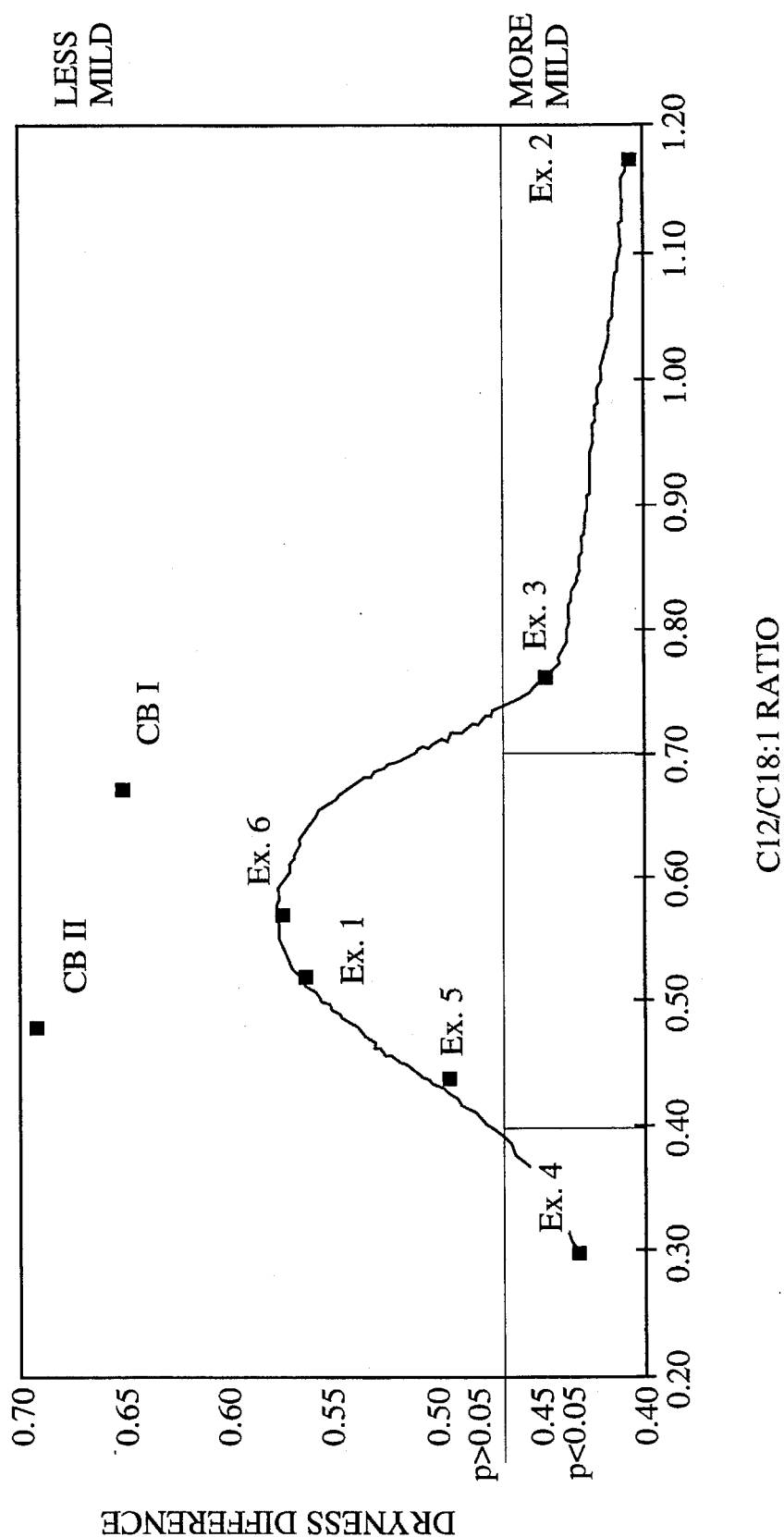

This figure represents the relative mildness (the lower the better) of Examples 1 through 6 as related to CB I and CB II.

FIG. 2

This figure represents the degree of skin dryness as a function of the ratio of C12 soap to C18:1 soap.

SUMMARY OF THE INVENTION

The present invention provides a mild, lathering personal cleansing soap bar composition comprising by weight of the bar: from 30 to 85 parts of a mixture of tailored fatty acid soaps, from 0 to 30 parts lathering synthetic detergent/surfactant and from 5 to 35 parts of water. The tailored fatty acid soap mixture of this invention comprises:

I. from 50% to 85% is saturated fatty acid soap selected from the group consisting of: myristic, palmitic, and stearic acid soaps and mixtures thereof; and II. from 15% to 50% is mixture of oleic (C18:1) and lauric acid (C12) soaps; including from 0 to 10% minor fatty acid soaps selected from the group consisting of: C8, C10, C18:2; and mixtures thereof;

and wherein said lauric and oleic soaps have a ratio of either 0.1:1 to 3:1; and wherein said tailored fatty acid soap mixture is about 65% to about 95% sodium soap and from about 5% to about 35% magnesium soap.

DETAILED DESCRIPTION OF THE INVENTION

The present invention relates to a mild, lathering personal cleansing tailored soap bar composition comprising: from 30 to 85 parts (preferably 50 parts to 75 parts) of tailored fatty acid soap and from 5 to 35 parts (preferably 8 parts to 15 parts) of water. The tailored fatty acid soap comprises:

I. from 50% to 85% (preferably 55% to 75%, or 60% to 70%) saturated fatty acid soap selected from the group consisting of: myristic, palmitic, and stearic acid soaps and mixtures thereof; and II. from 15% to 50% (preferably 20% to 45%, or 25% to 40%) lathering soap selected from the group consisting of: oleic (C18:1) and lauric acid (C12) soaps including from 0 to 10% minor fatty acid soaps selected from the group consisting of: C8, C10, C18:2; and mixtures thereof; and wherein the soap is 65% to about 95% (preferably 75% to 95%, or 80% to 90%) sodium soap and from 5% to about 35% (preferably 8% to 25% or 10% to 20%) magnesium soap.

The tailored soap bar further contains: from 8 to 35 parts of said (II) lathering lauric and oleic soaps and minor soaps; wherein said lauric and oleic soaps having a ratio of 0.1:1 to 3:1. A highly preferred tailored fatty acid soap comprises lauric and oleic soaps at a ratio of about 0.2:1 to about 0.4:1. Another highly preferred tailored fatty acid soap surprisingly comprises lauric and oleic soaps at a ratio of about 0.6:1 to about 2:1; more preferably from 0.7:1 to about 1:1.

It is important to selectively balance the amount of lauric and oleic soaps to achieve good lather and mildness. More lather is realized at the higher end of the level (35 parts) and better mildness is realized at the lower (8 parts) end of the level.

The tailored bar further contains: from about 5 parts to 30 parts (preferably 9 parts to 20 parts) of said oleic soap with from 2 to 15 parts (preferably 5 parts to 12 parts) being said lauric soap and from zero to about 7 parts (preferably 1 part to 5 parts) of said minor (C8, C10, C18:2) soaps.

The tailored fatty acid soap preferably comprises sodium and magnesium soaps having a ratio of 10:1 to 3:1.

A minor amount of potassium soap can be used; but in some highly preferred bar potassium soap is avoided.

A preferred bar of the present invention is a freezer bar. The freezer bar composition comprises by weight of the bar: from 20 to 35 parts water, preferably 23 to 30 parts water. Freezer bar soaps are made using a process generally disclosed in U.S. Pat. No. 3,835,058, White, issued on Sep. 10, 1974. The following commonly assigned references are incorporated herein by reference: Tollens et al U.S. Pat. Appl. Ser. No. 07/959,876 Filed Oct. 13, 1992, allowed now U.S. Pat. No. 5,387,362; Moroney, et al, U.S. Pat. No. 5,264,144. Issued on Nov. 23, 1993; and French, et al, U.S. Pat. No. 5,264,145; issued on Nov. 23, 1993.

Milled and framed bars are made using processes generally disclosed in Small et al. U.S. Pat. Nos. 4,673,525, 4,812,258; Medcalf et al. U.S. Pat. No. 4,820,447, and U.S.

Pat. No. 5,328,632, Redd et al., issued on Jul. 12, 1994, incorporated herein by reference. The above methods of making soap bars can be substantially different in terms of levels of ingredients, equipment and processing conditions. Redd, et al., U.S. Pat. No. 5,328,632, issued on Jul. 12, 1994

The levels, parts, percentages and ratios herein are by weight unless otherwise specified.

Note that the levels of the tailored soaps are expressed herein both in terms of weight percent (wt. %) of the total soap as well as parts by weight of the bar.

The term "parts" is used to denote the level of an ingredient "by weight of the bar." E.g. the present invention relates to a mild, lathering personal cleansing soap bar composition "by weight of the bar" comprising: from 30 to 85 "parts" of tailored fatty acid soap, from 3 to 30 "parts" lathering synthetic detergent/surfactant and from 5 to 35 "parts" of water.

All numerical limits, ranges, ratios, etc., are approximations (abouts) unless otherwise specified. Within the scope of the invention, there are several different preferred embodiments.

The terms "tailored fatty acid soap," "total soap" and "total fatty acid soap" as used herein are the same, unless otherwise specified.

The term "insoluble" soap as used herein means a soap less soluble than sodium myristate (C14). The magnesium soaps are insoluble. See Soap Solubility Table 1.

TABLE 1

| | Solubility of Soaps, Molar, 25° C. | | |
|---|---|---|---|
| | Na | K | Mg |
| C12 | 0.11 | Freely | Insoluble |
| C18:1 | 0.49 | Freely | — |
| C14 | 0.004 | Freely | Insoluble |
| C16 | Insoluble | — | Insoluble |
| C18 | Insoluble | — | Insoluble |

The term "soap" as used herein includes the plural as well as the singular in terms of mixed ions and fatty acid chains unless otherwise specified.

The terms "coconut oil" (CNO); "palm kernel oil" (PKO); "palm oil stearin" (POS); and "tallow" (T) as used herein refers to a mixture of soaps having an approximate chain length distribution as usually defined in the literature; unless otherwise specified.

The term "triple pressed stearic" as used herein refers to fatty acids having an approximate chain length distribution of 55% palmitic and 45% stearic.

The term "relatively more soluble soap" as used herein means a soap of which the fatty chain length or level of unsaturation is such that it is more soluble than sodium myristate, or a soap that has the solubility on the order of sodium laurate or sodium oleate soaps.

The tailored fatty acid soap of this invention can be made in part by using pure chain fatty acids, or by using the proper levels and ratios of common fatty acid mixtures such as coconut, palm kernel oil, palm oil stearin, tallow, and triple pressed stearic. The preferred levels and ratios can vary with the levels of cation mixtures.

Free Fatty Acids

Free fatty acids are preferably used in the present invention. They correspond with the fatty acids used to make the soaps. The free fatty acids affect the lathering characteristics of the bars prepared in accordance with the present invention. The free fatty acids increase the creaminess of the lather; the bars of this invention can show a mildness improvement over bars without free fatty acids. Fatty acids provide an emollient effect which tends to soften the skin or otherwise improve feel-on-skin characteristics and scavenge any excess alkalinity.

Synthetic Detergent Surfactant

Bars contain synthetic detergent surfactant, preferably a mild lathering synthetic detergent surfactant for the enhancement of the tailored base soap characteristics of improved rinse feel, curd dispersion, lathering and mildness through substitution for more harsh soluble soaps.

The synthetic detergent surfactant is typically selected from the group consisting of: anionic, nonionic, amphoteric and zwitterionic synthetic detergents. Both low and high lathering and high and low water-soluble surfactants can be used in the bar compositions of the present invention. Suds boosting synthetic detergent surfactants and/or synthetic detergent surfactants that are known as good dispersants for soap curds that are formed in hard water, are particularly desirable.

Examples include the water-soluble salts of organic, sulfonic acids and of aliphatic sulfuric acid esters, that is, water-soluble salts of organic sulfuric reaction products having in the molecular structure an alkyl radical of from 10 to 22 carbon atoms and a radical selected from the group consisting of sulfonic acid and sulfuric acid ester radicals.

Synthetic sulfate detergents of special interest are the normally solid alkali metal salts of sulfuric acid esters of normal primary aliphatic alcohols having from 10 to 22 carbon atoms. Thus, the sodium and potassium salts of alkyl sulfuric acids obtained from the mixed higher alcohols derived by the reduction of tallow or by the reduction of coconut oil, palm oil, palm kernel oil, palm oil stearin, babassu kernel oil or other oils of the lauric oil group can be used herein.

Other aliphatic sulfuric acid esters which can be suitably employed include the water-soluble salts of sulfuric acid esters of polyhydric alcohols incompletely esterified with high molecular weight soap-forming carboxylic acids. Such synthetic detergents include the water-soluble alkali metal salts of sulfuric acid esters of higher molecular weight fatty acid monoglycerides such as the sodium and potassium salts of the coconut oil fatty acid monoester of 1,2-hydroxypropane-3-sulfuric acid ester, sodium and potassium monomyristoyl ethylene glycol sulfate, and sodium and potassium monolauroyl diglycerol sulfate.

The synthetic surfactants and other optional materials useful in conventional cleaning products are also useful in the present invention. In fact, some ingredients such as certain hygroscopic synthetic surfactants which are normally used in liquids and which are very difficult to incorporate into normal cleansing bars are very compatible in the bars of the present invention. Thus, essentially all of the known synthetic surfactants which are useful in cleansing products are useful in the compositions of the present invention. The cleansing product patent literature is full of synthetic surfactant disclosures.

It is noted that surfactant mildness can be measured by a skin barrier destruction test which is used to assess the irritancy potential of surfactants. In this test the milder the surfactant, the less the skin barrier is destroyed. Skin barrier destruction is measured by the relative amount of radio-labeled water (3H-H20) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, Small et at., issued Jun. 16, 1987, incorporated herein by reference. These references disclose a mild alkyl glyceryl ether sulfonate (AGS) surfactant based synbar comprising a "standard" alkyl glyceryl ether sulfonate mixture and define the criteria for a "mild surfactant." Barrier destruction testing is used to select mild surfactants. Some preferred mild synthetic surfactants are disclosed in the above Small et al. and Rys et al. patents. Some specific examples of preferred surfactants are used in the Examples herein.

Some examples of good mild, lather-enhancing, synthetic detergent surfactants are, e.g., sodium lauroyl sarcosinate, alkyl glyceryl ether sulfonate (AGS), sulfonated fatty esters, and sulfonated fatty acids. Numerous examples of other surfactants are disclosed in the patents incorporated herein by reference. They include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates.

Alkyl chains for these other surfactants are C8–C22, preferably C10–C18. Alkyl glycosides and methyl glucose esters are preferred mild nonionics which can be mixed with other mild anionic or amphoteric surfactants in the compositions of this invention. Alkyl polyglycoside detergents are useful lather enhancers.

Normally the soap/synthetic bars are prepared to contain a ratio of soap to synthetic detergent of from about 3:1 to about 25:1. The choice of suitable ratios will depend upon the particular synthetic detergent, the desired performance and physical characteristics of the finished bar, temperature, moisture and like processing considerations. A preferred ratio is from about 4:1 to about 7:1.

THE LATHERING SURFACTANT

The lathering surfactant is defined herein as a synthetic surfactant or mixes thereof that when combined has (have) an equilibrium surface tension of between 15 and 50 dynes/cm, more preferrably between 20 and 45 dynes/cm as measured at the CMC (critical micell concentration) at 25° C. Some surfactant mixes can have surface tensions lower than of its components.

TABLE OF SOME SYNTHETIC SURFACTANTS SURFACE TENSION*

| Surfactant (dynes/cm) | Surface tension at CMC |
| --- | --- |
| Anionics | |
| Sodium Dodecane Sulfonate | 43 |
| Potassium Dodecane Sulfonate | 38 |
| Sodium Dodecyl Sulfate | 40 |
| Sodium Tetradecyl Sulfate | 35 |
| Sodium hexadecyl Sulfate | 37 |

-continued

TABLE OF SOME SYNTHETIC SURFACTANTS SURFACE TENSION*

| Surfactant (dynes/cm) | Surface tension at CMC |
| --- | --- |
| Sodium Dodeceth-2 Sulfate | 42 |
| Sodium Decyl Benzene Sulfonate | 48 |
| Sodium Dodecyl Benzene Sulfonate | 47 |
| Sodium Hexadecyl Benzene Sulfonate | 45 |
| Cationics | |
| Tetradecyl Trimethyl Anmonium Bromide | 41 |
| Dodecyl Trimethyl Ammonium Methane Sulfonate | 39 |
| Zwitterionics | |
| Dodecyl Betaine | 33 |
| Hexadecyl Betaine | 35 |
| Dodecyl Benzyl methyl Ampho Acetate | 33 |
| Nonionics | |
| 1,2 Dodecyldiol | 23 |
| 1,3 Pentadecyldiol | 27 |
| Hexeth-6 | 32 |
| Deceth-6 | 30 |
| Dodeceth-3 | 28 |
| Dodeceth-12 | 40 |
| Hexadeceth-6 | 32 |
| Hexadeceth-21 | 45 |
| Nonoxynol-10 | 31 |
| Nonoxynol-30 | 41 |
| Dimethicone copolyol | 21–22 |

*As calculated from Surfactants and Interfacial Phenomena by Rosen, Wiley, 1988)

TABLE OF SOME PREFERRED SURFACTANTS SURFACE TENSION**

| Surfactant | Surface tension (dynes/cm) |
| --- | --- |
| C12–C14 Glycerylether sulfonate | 47 |
| Sodium Lauryl Isethionate | 42 |
| Sodium Coco Isethionate | 42 |
| Sodium Stearyl Isethionate | 72 |
| Sodium Ether (3) Sulphate | 47 |
| Sodium Coco Taurate | 43 |
| Sodium Lauryl Sarcosinate | 42 |

**Measured on Kruss BP-10 Dynamic surface tensiometer, these measurements were not equilibrium, nor at the CMC. Equilibrium measurements are typically lower than Dynamic.

Anionic surfactants useful herein include acyl isethionates, acyl sarcosinates, alkylglycerylether sulfonates, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphonate, the alkyl ether sulfates (with 1 to 12 ethoxy groups), and mixtures thereof, wherein said surfactants contain C8 to C22 alkyl chain. The anionic surfactant is more preferred at about 8 parts to about 30 parts, selected from the group consisting of acyl isethionate, acyl sarcosinates, alkyl sulfosuccinates, alkylglycerylether sulfonates, methylacyl taurates, alkyl ether sulfates, alkyl sulfates, alkyl phosphate esters and mixtures thereof, wherein said surfactants contain C8 to C18 alkyl chains and wherein the counterion is selected from the group consisting of: Na, K, NH4, N(CH2CH2OH)3.

Cationic synthetic surfactant cannot serve as the sole surfactant in this product, but are preferred as a co-surfactant at a lower level of from about 0.5 parts to about 6 parts, by weight. The more preferred types of cationic surfactants are selected from the group consisting: alkyl trimonium chloride and methosulfate, and dialkyldimonium chloride and methyl sulphate, and alkyl alkonium chloride and methyl suphate and mixtures thereof. These surfactants contain C12 to C24 carbon atoms per alkyl chain. The most preferred cationic is selected from the group consisting of stearylkonium chloride, stearyltrimonium chloride, Di-stearyl-dimonium chloride, and mixtures thereof.

Polymers

A highly preferred embodiment of the present invention contains a polymeric skin mildness aid. Polymeric skin mildness aids are disclosed in the Small et al. and Medcalf et al. patents. (U.S. Pat. Nos. 4,673,525; 4,812,258; and 4,820,447 incorporated herein by reference.) The cationic synthetic polymers useful in the present invention are cationic polyalkylene imines, ethoxypolyalklene imines, and poly[N-[-3-( dimethylammonio )propyl]-N'-[3-( ethyleneoxyethylene dimethylammonio)propyl]urea dichloride] the latter of which is available from Miranol Chemical Company, Inc. under the trademark of Miranol A-15, CAS Reg. No. 68555-36-2.

Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are JAGUAR C-14-S, C-15 and C-17 sold by the successor of the Celanese Corporation. In order to achieve the benefits described in this invention, the polymer must have characteristics, either structural or physical which allow it to be suitably and fully hydrated and subsequently well incorporated into the soap matrix.

Other Ingredients

The bar soap compositions of the present invention can contain other additives commonly included in toilet bars such as perfumes, other fillers, sanitizing or antimicrobial agents, dyes, and the like.

Preservatives, e.g., sodium ethylenediaminetetraacetate (EDTA), generally at a level of less than 1 parts of the composition, can be incorporated in the cleansing products to prevent color and odor degradation. Antibacterials can also be incorporated, usually at levels up to 1.5 parts. The above patents disclose or refer to such ingredients and formulations which can be used in the bars of this invention, and are incorporated herein by reference.

Some bars of this invention contain at least about 1 parts of another bar ingredient selected from: moisturizers, colorants, solvents, fillers, polymeric skin feel and mildness aids, perfumes, preservatives, and mixtures thereof.

Compatible salt and salt hydrates can be incorporated into the formulation. Some preferred salts are sodium chloride, sodium sulfate, disodium hydrogen phosphate, sodium pyrophosphate, sodium tetraborate. Sodium chloride is kept below 2.0 parts by weight of the bar, preferably less than 1 parts.

EXAMPLES

The following Examples illustrate the practice of this invention and are not intended to be limiting. All percentages, parts and ratios herein are by weight unless otherwise specified. All levels and ranges, temperatures, results etc., used herein are approximations unless otherwise specified. The free fatty acids used in the examples are used at about the same ratio as that of the fatty acid soaps. The soaps are made in situ, unless otherwise specified. The levels of soaps are given as a total soap weight percent (wt. %), as well as parts by bar weight.

The milled soap bar compositions are mixed at a temperature of about 190° F. (88° C.) and pumped into a heat exchanger where the temperature of the mix is heated to about 240° F. (115° C.). The heated mixture is dried either atmospherically or with vacuum; flaked, combined with minors, milled, extruded, bar plugs are cut and deposited on a chilled roll and the final bars are then stamped. See the Small et al. or Medcalf et al. patents for milled bar soap processing details. (U.S. Pat. Nos. 4,673,525; 4,812,258; and 4,820,447 incorporated herein by reference.)

The exaggerated forearm wash test is a modified Lukacovic, Dunlap, Michaels, Visscher, and Watson: "Forearm wash test to evaluate the clinical mildness of cleansing products," J. Soc. Cosmet. Chem., 39, 355–366 (November/December 1988). One week of testing is used instead of two weeks.

TABLE 1

| | Prior Art Bars | | | |
| | CBI | | CBII | |
| | In Bar | In Soap | In Bar | In Soap |
|---|---|---|---|---|
| C8-caprylic | 1.3 | 2.1 | 0.8 | 1.7 |
| C10-capric | 1.1 | 1.8 | 0.7 | 1.5 |
| C12-laurate | 12.8 | 20.0 | 6.8 | 13.7 |
| C14-myristate | 5.9 | 9.2 | 4.22 | 8.6 |
| C16 palmitate | 12.7 | 19.8 | 13.2 | 26.8 |
| C18-stearate | 11.1 | 17.3 | 9.3 | 18.8 |
| C18:1,2-oleate | 19.1 | 29.8 | 14.3 | 28.9 |
| Total Soap % | | 100 | | 100 |
| Total Soap Parts | 66.2 | | 54.1 | |
| Water | 8.0 | | 9.4 | |
| Synthetic (AGS for CB I & SCI for CB II) | 16.5 | | 23.0 | |
| NaCl | 3.3 | | 0.5 | |
| Perfume/color/etc. | 1.3 | | * | |
| Free Fatty Acid | 2.0 | | 9.0 | |
| Miscellaneous | 2.6 | | 7.1*includes perfume, color and misc. salts | |
| TOTAL BAR Soap % | 100 | | 100 | |
| C14;16;18 | * | 46.3† | * | 54.2 |
| C8;10;12;18:1 | * | 53.7† | * | 45.8 |
| Bar Parts | | | | |
| C8;10;12;18:1 | 34.4 | * | 22.6 | * |
| C18:1 | 19.1 | * | 14.3 | * |
| C12 | 12.8† | * | 6.8 | * |
| C8;10;18:2 | 2.5 | * | 1.6 | * |
| C12+18:1/other | 12.9† | * | 13.4 | * |
| Counterions: | | | | |
| —Na | * | 81.0 | * | 100† |
| —K | * | 0.0 | * | 0.0 |
| —Mg | * | 19.0 | * | 0.0 |
| Na+K | * | 81.0 | * | 100† |
| Na:K | * | none | * | none |
| Na:Mg | * | 4.3 | * | none† |

TABLE 1-continued

|  | Prior Art Bars | | | |
|---|---|---|---|---|
|  | CBI | | CBII | |
|  | In Bar | In Soap | In Bar | In Soap |
| K:Mg | * | 0.0 | * | none† |
| C12/C18:1 (<0.4 or >0.72) | 0.67† | | 0.48† | |

†This symbol denotes that the level is outside of the preferred level range for that ingredient.

TABLE 2

| Claims | Example 1 | | Example 5 | | Example 6 | |
|---|---|---|---|---|---|---|
| C8-caprylic | 0.5 | 0.8 | 0.4 | 0.6 | 0.5 | 0.7 |
| C10-capric | 0.5 | 0.8 | 0.4 | 0.6 | 0.5 | 0.7 |
| C12-laurate | 8.7 | 12.9 | 7.1 | 10.5 | 7.9 | 11.8 |
| C14-myristate | 3.8 | 5.7 | 3.3 | 4.9 | 3.6 | 5.3 |
| C16-palmitate | 29.8 | 44.2 | 31.2 | 46.4 | 30.0 | 44.8 |
| C18-stearate | 7.3 | 10.8 | 8.6 | 12.9 | 10.7 | 16.0 |
| C18:1,2-oleate | 16.8 | 24.9 | 16.1 | 24.0 | 13.9 | 20.7 |
| Total Soap (%) | | 100 | | 100 | | 100 |
| Total Soap | 70.9 | | 67.7 | | 67.7 | |
| H2O | 12.0 | | 12.0 | | 12.0 | |
| Synthetic (AGS) | 13.0 | | 16.0 | | 16.0 | |
| NaCl | 0.5 | | 0.6 | | 0.5 | |
| Perfume/color/etc. | 1.0 | | 1.0 | | 1.0 | |
| Free Fatty Acid | 2.0 | | 2.0 | | 2.0 | |
| Miscellaneous | 1.0 | | 1.0 | | 1.0 | |
| TOTAL Soap % | 100 | | 100 | | 100 | |
| C14;16;18 | * | 60.7 | * | 64.2 | * | 66.1 |
| C8;10;12;18:1 | * | 39.3 | * | 35.8 | * | 33.9 |
| Bar Parts: | | | | | | |
| C8;10;12;18:1 | 26.5 | | 24.0 | | 22.7 | |
| C18:1 | 16.8 | | 16.1 | | 13.9 | |
| C12 | 8.7 | | 7.1 | | 7.9 | |
| C8;10;18:2(0 to 7) | 8.3 | | 0.8 | | 11.7 | |
| Counterion-Na | | 82.0 | | 81.0 | | 82.0 |
| —Mg | | 18.0 | | 19.0 | | 18.0 |
| Na:Mg (20 to 1) | | 4.6 | | 4.3 | | 4.6 |
| C12/C18:1 (<0.4 or >0.72) | | 0.52† | | 0.44† | | 0.57† |

†This symbol denotes that the level is outside of the preferred level range for that ingredient.

TABLE 3

|  | Example 2 High Laurate | | Example 3 | |
|---|---|---|---|---|
|  | In Bar | In Soap | In Bar | In Soap |
| C8-caprylic | 0.7 | 1.1 | 1.4 | 2.1 |
| C10-capric | 0.7 | 1.1 | 1.1 | 1.6 |
| C12-laurate | 11.5 | 17.2 | 8.5 | 12.6 |
| C14-myristate | 4.8 | 7.2 | 3.9 | 5.8 |
| C16-palmitate | 25.9 | 38.8 | 29.5 | 43.6 |
| C18-stearate | 13.4 | 20.0 | 12.0 | 17.8 |
| C18:1,2-oleate | 9.8 | 14.7 | 11.1 | 16.5 |
| Total Soap % | | 100% | | 100% |
| Total Soap Parts | 67.6 | | 67.6 | |
| H2O | 12.0 | | 12.0 | |
| Synthetic (AGS) | 16.0 | | 16.0 | |
| NaCl | 0.6 | | 0.6 | |
| Perfume, etc. | 1.0 | | 1.0 | |
| Free Fatty Acid | 2.0 | | 2.0 | |
| Miscellaneous | 1.0 | | 1.0 | |
| TOTAL Parts | 100 | | 100 | |
| Salts: | | | | |
| C14;16;18 | * | 66.0 | * | 67.3 |
| C8;10;12;18:1 | * | 34.0 | * | 32.7 |
| As Bar: | | | | |
| C8;10;12;18:1 (8 to 35) | 22.8 | * | 22.1 | * |
| C18:1 (0 to 25) | 9.8 | * | 11.1 | * |
| C12 (0 to 12) | 11.5 | * | 8.5 | * |
| C8;10;18:2 (0 to 7) | 1.5 | * | 2.5 | * |
| C12+18:1+ Mc (1 to 10) | 14.5 | * | 7.8 | * |
| Counterion: | | | | |
| —Na | | 81.0 | | 81.0 |
| —Mg | | 19.0 | | 19.0 |
| Na:Mg | | 4.3 | | 4.3 |
| C12/C18:1 (<0.4 or >0.7) | | 1.17 | | 0.76 |

Example 4 is significantly milder than the Comparative Bar I (CB-I), in an exaggerated forearm wash test.

TABLE 4

|  | Example 4 (Lo C12/Hi 18:1) | |
|---|---|---|
|  | In Bar | In Soap |
| C8-caprylic | 0.3 | 0.5 |
| C10-capric | 0.3 | 0.5 |
| C12-laurate | 5.6 | 8.3 |
| C14-myristate | 2.8 | 4.1 |
| C16 palmitate | 32.9 | 49.0 |
| C18-stearate | 6.7 | 9.9 |
| C18:1,2-oleate | 18.6 | 27.7 |
| % of Total Soap | — | 100 |
| Total Soap Bar Parts | 67.7 | |
| Water | 12.0 | |
| Synthetic (Preferably AGS) | 16.0 | |
| NaCl | 0.6 | |
| Perfume/color/etc. | 1.0 | |
| Free Fatty Acid | 2.0 | |
| Miscellaneous | 1.0 | |
| TOTAL Soap % | 100 | |
| C14;16;18 | * | 63.1 |
| C8;10;12;18:1 | * | 36.9 |
| Bar Parts | | |
| C8;10;12;18:1 | 24.8 | * |
| C18:1 | 18.6 | * |
| C12 | 5.6 | * |

TABLE 4-continued

| | Example 4 (Lo C12/Hi 18:1) | |
|---|---|---|
| | In Bar | In Soap |
| C8;10;18:2 | 0.6 | * |
| Counterions: | | |
| —Na (65 to 97) | * | 81.0 |
| —Mg (3 to 35) | * | 19.0 |
| Na:Mg (20 to 1) | * | 4.3 |
| C12/C18:1 (<0.4 or >0.72) | 0.30 | |

Tables 1 and 4

Example 4 bar is a superior bar. It is very mild and its lather is comparable to the harsher CB I and CB II of Table 1. It also imparts the same rinsing characteristics as superior rinsing CB I. Example 4 contains Magnesium soap and Sodium Alkyl Glycerol Sulfonate as in CB I. Example 4 contains a lower level of C12 (laurate) soap than CB I with a comparable level of C18:1. The total soap levels are comparable. The C12/C18:1 ratio is however 0.67 for CB I versus 0.30 for Example 4. As compared to CB II, Example 4 slightly lower levels of C12 soap and a higher level of C18:1 soap. The C12/C18:1 ratio of Example 4 is within the required range of <0.4 whereas CB II falls within the less preferred range (0.4 to 0.72) with a C12/C18:1 of 0.48. Example 4 is milder than CBII; yet, Example 4 contains more total soap than CBII.

Table 2

Table 2 contains the compositions of bars which are slightly milder than CB I and CB II in clinical testing. Ex. 1, 5 and 6 demonstrate comparable lathering characteristics to the preferred bar (Example 4) however rinse feel more closely resembles CB II than the superior rinsing of CB I.

Table 3

The compositions of Examples 2 and 3 are listed in Table 3. Examples 2 and 3 demonstrate statistically significant ($p<0.05$) superior mildness as compared to CB II. These bars are unique in that they both contain higher levels of C12 soap, which was previously thought to be the dominant cause of harshness; in addition, these bars contain higher levels of total soap than CB II. These bars however are again unique in that they contain lower levels of C18:1 soap. It is this ratio of C12/C18:1 soap being greater than 0.70 yields a lathering, soap/synthetic bars of unsurpassed and surprising mildness.

TABLE 5

| A FREEZER BAR | | |
|---|---|---|
| | Example 7 In Bar | In Soap |
| C8-caprylic | 1.2 | 2.11 |
| C10-capric | 0.9 | 1.63 |
| C12-laurate | 7.2 | 12.63 |
| C14-myristate | 3.5 | 6.08 |
| C16-palmitate | 26.2 | 45.71 |
| C18-stearate | 8.2 | 14.37 |
| C18:1,2-oleate | 9.7 | 17.01 |
| C18:2 | 1.2 | 2.02 |

TABLE 5-continued

| A FREEZER BAR | | |
|---|---|---|
| | Example 7 In Bar | In Soap |
| Total Soap (%) | | 100 |
| Total Soap Parts | 57.78 | |
| H2O | 27 | |
| Synthetic (AGS) | 10 | |
| NaCl | 0.77 | |
| Perfume/color/etc. | 0.5 | |
| Free Caustic | none | |
| Free Fatty Acid | 3 | |
| Miscellaneous | 0.95 | |
| Bar Parts | TOTAL | 100 |
| C14;16;18 | * | * | 66.2 |
| C8;10;12;18:1 | * | * | 33.4 |
| As Bar | | | |
| C8;10;12;18:1 | * | 19.1 | * |
| C18:1 | * | 9.7 | * |
| C12 | * | 7.2 | * |
| C8;10;18:2 | * | 4.2 | |
| Counterion | | | |
| —Na | 92 to 64 | 90.0 | |
| —Mg | 8 to 18 | 10.0 | |
| Na:Mg | 20 to 1 | 9.0 | |
| C12/C18:1 | <.4 or >.7 | 0.74 | |

The freezer bar composition is set out in Table 5 as Example 7. This bar is unique in that lathering is comparable to the harsher CBI listed in Table 1. The mildness of Example 7 is comparable to the Examples of Invention (Examples 2,3 and 4) and has a laurate/oleate ration of 0.74. The composition of Example 7 is similar to that of Example 3 except that Example 7 contains 27% Water which is preferred for a Freezer bar. Example 3 contains 12% water which is preferred for a milled bar.

The personal cleansing bars which are made with the carefully tailored fatty acid soap and with the mixed counterions (Mg and Na) and selected fatty acids of the present invention are surprisingly milder that comparable bars that are made with prior art base soaps. The bars of the present invention are good lathering. Their lathers are good rinse feel lathers. Their processability is good and their wear rates are good. Their smear rates are also good. The bars of the present invention cleanse the skin gently, causing little or no irritation and with less drying.

What is claimed is:

1. A mild, lathering personal cleansing soap bar composition by weight of the bar comprising: from 30 to 85 parts tailored fatty acid soap, from 3 parts to 30 parts synthetic surfactant, and from 5 to 35 parts of water; wherein said tailored fatty acid soap by weight of total soap comprises:

I. from 50% to 85 % of total soap is saturated fatty acid soap selected from the group consisting of: myristic, palmitic, and stearic acid soaps and mixtures thereof; and II. from 15% to 50% by weight of total soap is: oleic ($C_{18:1}$) and lauric acid ($C_{12}$) soaps and minor fatty acid soaps selected from the group consisting of: $C_8$, $C_{10}$, $C_{18:2}$; and mixtures thereof; and wherein said lauric and oleic soaps have a ratio of 0.1:1 to 3:1 and wherein said tailored fatty acid soap mixture is about 65% to about 95% sodium soap and from about 5% to about 35 % magnesium soap, and wherein said soap bar composition is essentially free of potassium soap.

2. The mild, lathering personal cleansing soap bar composition of claim 1 wherein said composition is from 50 to 75 parts said tailored fatty acid soap, from 3 parts to 30 parts said synthetic surfactant, and from 8 to 15 parts of water; wherein said tailored fatty acid soap by weight of total soap comprises:

I. from 55% to 75% of total soap is said saturated fatty acid soap selected from the group consisting of: myristic, palmitic, and stearic acid soaps and mixtures thereof, and II. from 20% to 45% by weight of total soap is: said oleic (C18:1) and lauric acid (C12) soaps and minor fatty acid soaps selected from the group consisting of: C8, C10, C18:2; and mixtures thereof; and wherein said tailored fatty acid soap mixture is about 75% to about 95% said sodium soap and from about 8% to about 25% said magnesium soap.

3. The mild, lathering personal cleansing soap bar composition of claim 2 wherein said tailored fatty acid soap by weight of total soap comprises:

I. from 60% to 70% of total soap is said saturated fatty acid soap selected from the group consisting of: myristic, palmitic, and stearic acid soaps and mixtures thereof; and II. from 25% to 40% by weight of total soap is: said oleic (C18:1) and lauric acid (C12) soaps and minor fatty acid soaps selected from the group consisting of: C8, C10, C18:2; and mixtures thereof, and wherein said tailored fatty acid soap mixture is about 80% to about 90% said sodium soap and from about 10% to about 20 % said magnesium soap.

4. The mild, lathering personal cleansing soap bar composition of claim 1 wherein said Na soap level is from 65% to 90%, by weight of said total soap; and the Mg soap level is from 10% to 25%, by weight of the total soap; and wherein the bar comprises:

A. from 60 parts to 85 parts, of said total tailored fatty acid soap;

B. from 1 parts to 15 parts, of free fatty acid;

C. from 5 parts to 30 parts, of said water;

D. from 8 parts to 15 parts said synthetic surfactant.

5. The mild, lathering personal cleansing soap bar composition of claim 1 wherein said lauric and oleic soaps has a ratio of about 0.2:1 to about 0.4: 1.

6. The mild, lathering personal cleansing soap bar composition of claim 1 wherein said lauric and oleic soaps ratio of is about 0.7:1 to about 2:1.

7. The bar of claim 1 wherein said lauric and oleic soaps ratio of is about 0.7:1 to about 2:1; and wherein said bar contains from 30 to 85 parts said tailored fatty acid soap, from 5 parts to 20 parts said synthetic surfactant, and from 8 to 15 parts of water and wherein said tailored fatty acid soap mixture is about 80% to about 90% sodium soap and from about 10% to about 20% magnesium soap.

8. The mild, lathering personal cleansing soap bar composition of claim 1 wherein said bar is a milled bar.

9. A mild, lathering personal cleansing soap bar composition by weight of the bar comprising: from 30 to 85 parts tailored fatty acid soap, from 3 parts to 30 parts synthetic surfactant, and from 5 to 35 parts of water; wherein said tailored fatty acid soap by weight of total soap comprises:

I. from 50% to 85% is saturated fatty acid soap selected from the group consisting of: myristic, palmitic, and stearic acid soaps and mixtures thereof, and II. from 15% to 50% by weight of total soap is: oleic (C18:1) and lauric acid (C12) soaps and minor fatty acid soaps selected from the group consisting of: C8, C10, C18:2; and mixtures thereof, and wherein said lauric and oleic soaps have a ratio of and wherein said tailored fatty acid soap mixture is about 65% to about 95% sodium soap and from about 5% to about 35% magnesium soap; and wherein said bar is essential free of potassium soap.

10. A mild, lathering personal cleansing soap bar composition by weight of the bar comprising: from 30 to 85 parts tailored fatty acid soap, from 3 parts to 30 parts synthetic surfactant, and from 5 to 35 parts of water; wherein said tailored fatty acid soap by weight of total soap comprises:

I. from 50% to 85% is saturated fatty acid soap selected frozen the group consisting of: myristic, palmitic, and stearic acid soaps and mixtures thereof; and II. from 15% to 50% by weight of total soap is: oleic ($C_{18:1}$) and lauric acid ($C_{12}$) soaps and from 0 to 10% minor fatty acid soaps selected from the group consisting of: $C_8$, $C_{10}$, $C_{18:2}$; and mixtures thereof; and wherein said tailored fatty acid soap mixture is about 65% to about 95% sodium soap and from about 5% to about 35% magnesium soap, and wherein said bar is essentially free of potassium soap.

11. A mild, lathering personal cleansing soap bar composition by weight of the bar comprising: from 30 to 85 parts tailored fatty acid soap, from 3 parts to 30 parts synthetic surfactant, and from 5 to 35 parts of water; wherein said tailored fatty acid soap by weight of total soap comprises:

I. from 50% to 85% is saturated fatty acid soap selected from the group consisting of: myristic, palmitic, and stearic acid soaps and mixtures thereof; and II. from 15% to 50% by weight of total soap is: oleic ($C_{18:1}$) and lauric acid ($C_{12}$) soaps and minor fatty acid soaps selected from the group consisting of: $C_8$, $C_{10}$, $C_{18:2}$; and mixtures thereof; and wherein said lauric and oleic soaps have a ratio of 0.2:1 to about 0.4:1 and wherein said tailored fatty acid soap mixture is about 65% to about 95% sodium soap and from about 5% to about 35 magnesium soap, and wherein said soap bar composition is essentially free of potassium soap.

12. A mild, lathering personal cleansing soap bar composition by weight of the bar comprising: from 30 to 85 parts tailored fatty acid soap, from 3 parts to 30 parts synthetic surfactant, and from 5 to 35 parts of water; wherein said tailored fatty acid soap by weight of total soap comprises:

I. from 50% to 85% is saturated fatty acid soap selected from the group consisting of: myristic, palmitic, and stearic acid soaps and mixtures thereof; and II. from 15% to 50% by weight of total soap is: oleic ($C_{18:1}$) and lauric acid ($C_{12}$) soaps and minor fatty acid soaps selected from the group consisting of: $C_8$, $C_{10}$, $C_{18:2}$; and mixtures thereof; and wherein said lauric and oleic soaps have a ratio of about 0.7:1 to about 2:1 and wherein said tailored fatty acid soap mixture is about 65% to about 95% sodium soap and from about 5% to about 35% magnesium soap, and wherein said soap bar composition is essentially free of potassium soap.

13. The mild, lathering personal soap bar composition of claim 1 wherein said bar contains an antibacterial agent.

14. The mild, lathering personal cleansing soap bar composition of claim 13 wherein said bar is a milled bar.

* * * * *